United States Patent
Valdevit et al.

(10) Patent No.: US 9,228,916 B2
(45) Date of Patent: Jan. 5, 2016

(54) SELF CALIBRATING MICRO-FABRICATED LOAD CELLS

(71) Applicant: THE REGENTS OF THE UNIVERSITY OF CALIFORNIA, Oakland, CA (US)

(72) Inventors: Lorenzo Valdevit, Irvine, CA (US); Kivanc Azgin, Ankara (TR)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 174 days.

(21) Appl. No.: 13/842,152

(22) Filed: Mar. 15, 2013

(65) Prior Publication Data

US 2013/0276510 A1    Oct. 24, 2013

Related U.S. Application Data

(60) Provisional application No. 61/624,156, filed on Apr. 13, 2012.

(51) Int. Cl.
   *G01L 25/00* (2006.01)
   *G01L 1/00* (2006.01)
   *G01L 1/10* (2006.01)
   *G01N 33/20* (2006.01)

(52) U.S. Cl.
   CPC . *G01L 25/00* (2013.01); *G01L 1/00* (2013.01); *G01L 1/10* (2013.01); *G01N 33/203* (2013.01)

(58) Field of Classification Search
   CPC .......... G01C 19/5607; G01C 19/5712; G01C 19/5614; G01P 15/097; G01P 15/125; G01P 15/14; G01L 1/10; G01L 25/00
   See application file for complete search history.

(56) References Cited

U.S. PATENT DOCUMENTS

| | | | | |
|---|---|---|---|---|
| 6,035,694 A * | 3/2000 | Dupuie et al. | ................. | 73/1.38 |
| 6,481,283 B1 * | 11/2002 | Cardarelli | .................. | 73/504.02 |
| 7,114,366 B1 * | 10/2006 | Jones et al. | .................... | 73/1.01 |
| 2005/0284221 A1 * | 12/2005 | Danisch et al. | ................. | 73/488 |
| 2006/0005603 A1 * | 1/2006 | Chau et al. | ..................... | 73/1.38 |
| 2006/0161363 A1 * | 7/2006 | Shibasaki et al. | .............. | 702/94 |
| 2009/0064781 A1 * | 3/2009 | Ayazi | ................. | G01C 19/5719 73/504.12 |
| 2009/0246935 A1 * | 10/2009 | Kawai et al. | .................. | 438/458 |
| 2009/0293583 A1 * | 12/2009 | Stewart et al. | ................. | 73/1.38 |
| 2010/0024548 A1 * | 2/2010 | Cardarelli | .................. | 73/504.13 |
| 2011/0014776 A1 * | 1/2011 | Akiyama et al. | ............. | 438/458 |
| 2012/0198934 A1 * | 8/2012 | Cardarelli | ................. | 73/504.02 |
| 2012/0318060 A1 * | 12/2012 | Ruby | ........................ | 73/514.32 |

FOREIGN PATENT DOCUMENTS

WO    WO 02065055 A2 *  8/2002

OTHER PUBLICATIONS

Azgin et al., "A Resonant Tuning Fork With Unprecedented Combination of Resolution and Range", 2011 IEEE 24th International Conference on Micro Electro Mechanical Systems, Jan. 23-27, 2011.*

Torrents et al., "MEMS Resonant Load Cells for Micro-mechanical Test Frames: Feasibility Study and Optimal Design", Journal of Micromechanics and Microengineering, vol. 20, No. 12, Nov. 8, 2010.*

* cited by examiner

*Primary Examiner* — David A Rogers
(74) *Attorney, Agent, or Firm* — One LLP

(57) ABSTRACT

Self calibrating micro-fabricated load cells are disclosed. According to one embodiment, a self calibrating load cell comprises a resonant double ended tuning fork force sensor and a phase locked loop circuit for detection of frequency changes upon external load application to the resonant double ended tuning fork force sensor.

18 Claims, 18 Drawing Sheets

600

SELF CALIBRATING MICRO-FABRICATED LOAD CELLS

The present application claims the benefit of and priority to U.S. Provisional Application No. 61/624,156 titled "SELF CALIBRATING MICRO-FABRICATED LOAD CELLS," filed on Apr. 13, 2012, which is hereby incorporated by reference in its entirety.

FIELD

The embodiments relate generally to load cells and more particularly to resonant MEMS load cells for use in micromechanical test frames for the characterization of small-scale materials and structures.

BACKGROUND

The motivation for the development of novel micro-mechanical test frames is grounded in the recent development of micro-architected cellular materials. Novel advances in their manufacturing and optimal design urgently require the development of versatile and accurate experimental techniques for mechanical characterization at the unit cell level. Wide force and displacement ranges are generally necessary, while nN and nm resolutions are needed to capture small-scale phenomena. The ideal micromechanical test frame should be capable of measuring forces with resolutions in the 1-100 nN range with potentially large displacements (~1 mm), allow optical (or SEM) access to the test coupon with potential for strain mapping (via Digital Image Correlation), be readily reconfigurable and adaptable to microstructures of a variety of shapes and sizes.

On-chip MEMS test frames have already been demonstrated. Although excellent for alignment purposes and resolutions, they lack the displacement range and versatility discussed above. A hybrid micro-test frame (comprising an off-chip actuator and a MEMS sensor) with the desired displacement range and resolution was recently introduced, but the compliant sensor limited the achievable force range. A limited number of fully integrated nanoindenter/SEM combinations exist today; but such devices are unique, highly customized, extremely expensive, and often limited in the maximum achievable displacement and/or force range.

The dependence of the resonant frequencies of structures on internal stresses had found applications in vibrating cylinder pressure transducers as early as the mid-1960s. A decade later, separation of the sensor element and the pressure chamber was shown to improve the resolution, resulting in one of the first demonstrations of axially loaded resonant load cells. This approach was subsequently applied to micro accelerometers and precision scales. The use of resonant force sensors for material characterization was first implemented at the macro scale. More recent developments in silicon micromachining techniques and brilliant yet simple design solutions for actuation and detection mechanisms led to micromachined resonant force sensors, at first designed for accelerometer applications. The DETF structure is later proven to be a feasible design for a number of other micro sensor applications.

The governing mechanics of DETF sensors is well documented, as is their most recent application to accelerometers and gyroscopes.

SUMMARY

Self calibrating micro-fabricated load cells are disclosed. According to one embodiment, a self calibrating load cell comprises a resonant double ended tuning fork force sensor and a phase locked loop circuit for detection of frequency changes upon external load application to the resonant double ended tuning fork force sensor.

The systems, methods, features and advantages of the invention will be or will become apparent to one with skill in the art upon examination of the following figures and detailed description. It is intended that all such additional methods, features and advantages be included within this description, be within the scope of the invention, and be protected by the accompanying claims. It is also intended that the invention is not limited to require the details of the example embodiments.

BRIEF DESCRIPTION

The accompanying drawings, which are included as part of the present specification, illustrate the presently preferred embodiment and, together with the general description given above and the detailed description of the preferred embodiment given below, serve to explain and teach the principles of the present invention.

Figure 1:
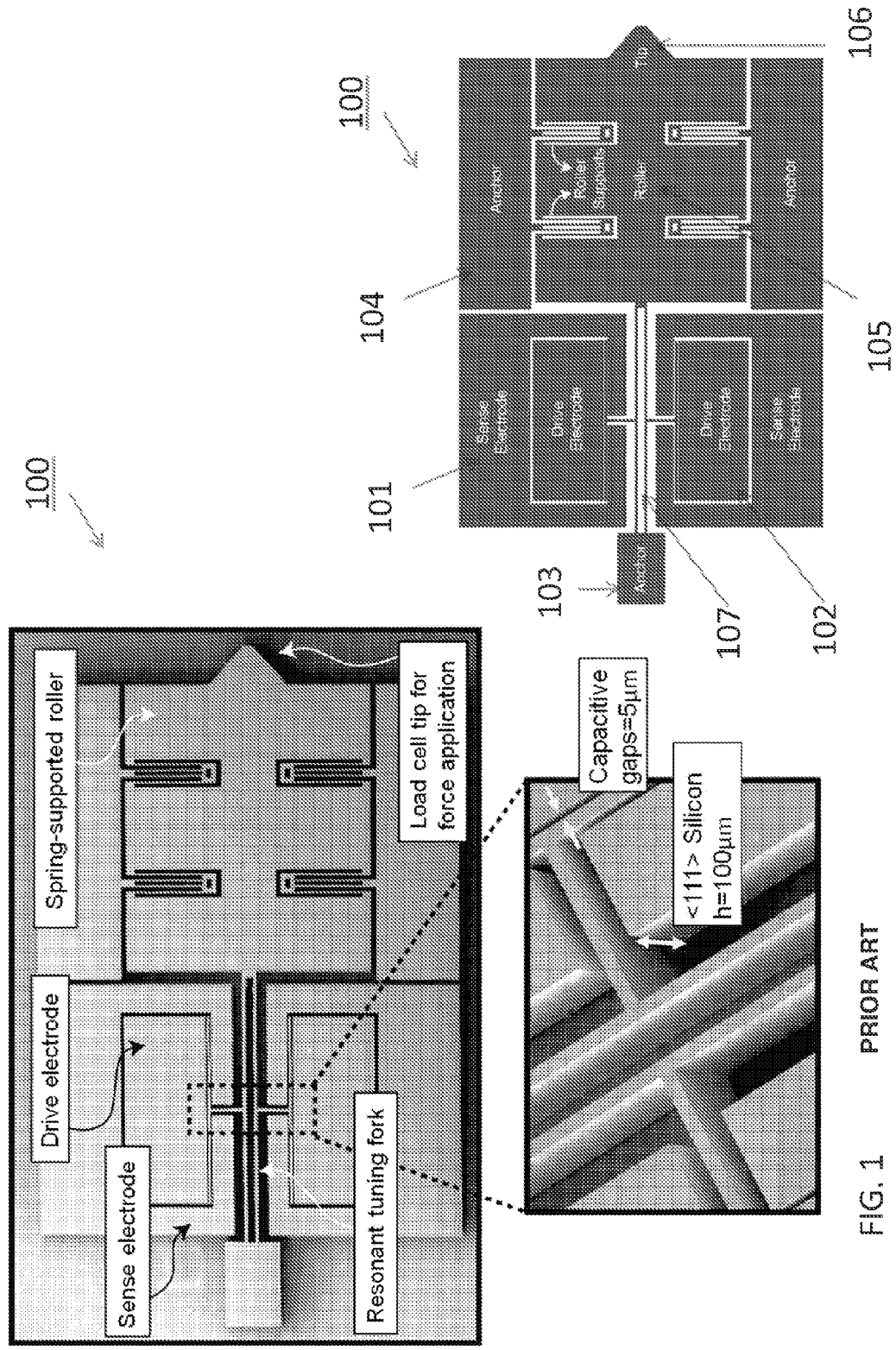
FIG. 1 illustrates an exemplary force sensor for use with the present system, according to one embodiment.

It should be noted that the figures are not necessarily drawn to scale and that elements of similar structures or functions are generally represented by like reference numerals for illustrative purposes throughout the figures. It also should be noted that the figures are only intended to facilitate the description of the various embodiments described herein. The

DETAILED DESCRIPTION

The embodiments provided herein are directed to a manufacturing process and a self-calibration procedure for the practical use of MEMS resonant sensors as ultra-sensitive load cells. The embodiments enable the cost-effective fabrication and implementation of load cells with unprecedented combination of resolution and range. Such load cells can be mounted on hybrid micro-mechanical test frames or integrated with suitable on-chip actuators for the characterization of materials and structures at small scales.

In one embodiment, a resonant double-ended tuning fork (DETF) force sensor is provided with an experimentally demonstrated resolution of 7 nN and a compressive load range of 0.085N, exceeding a dynamic range of 140 dB (100 parts per billion). The resonator has a scale factor of 216 kHz/N, a Q-factor exceeding 60,000 at 3 mTorr ambient pressure and a zero load resonant frequency of 47.6 kHz. The resonator is kept at resonance via a Phase Locked Loop (PLL) comprised of discrete elements. A self resonance scheme could also be employed for the same intention. The sensor is implemented with a Silicon-on-Insulator process with 100 µm silicon structural layer. The sensor and the complete readout circuit are fully embedded in a compact 65 mm×52 mm printed circuit board (PCB). The out-of-plane parasitic modes of the DETF are also investigated with FEM simulations and Laser Doppler Vibrometry experiments, and are verified to be outside of the device working range. The PCB is mounted on a microstage and coupled with an off-the-shelf displacement actuator to realize an economical, versatile and robust micro mechanical test frame with unprecedented combination of force and displacement resolution and range.

FIG. 1 illustrates an exemplary force sensor for use with the present system, according to one embodiment. An exemplary sensor element 100 is composed of a DETF resonator and a roller structure 105 attached to it. The sensor element 100 includes a sense electrode 101 and a drive electrode 102 situated on either side of a tuning fork 107. The geometric parameters of the device can be chosen to achieve optimal combinations of resolution and range.

An implementation of an exemplary device disclosed herein uses a 100 µm-thick <111> oriented single crystal silicon structural layer; other exemplary dimensions of the device are summarized in Table 1.

TABLE 1

Summary of exemplary geometric dimensions for one embodiment of the DETF presented herein.

| Dimension | Symbol | Value (µm) |
| --- | --- | --- |
| Tine length | $L_f$ | 964 |
| Tine width | $w_f$ | 10 |
| Capacitive plate length | $L_p$ | 680 |
| Capacitive plate width | $w_p$ | 10 |
| Capacitive gap | g | 5 |
| Connector length | $L_g$ | 120 |
| Connector width | $w_c$ | 10 |
| Device thickness | h | 100 |

Upon external axial force application (compressive or tensile), the natural frequency of the tines changes (decreases or increases, respectively), and this change is detected by means of a Phase Locked Loop (PLL) circuit described below.

Figure 2:
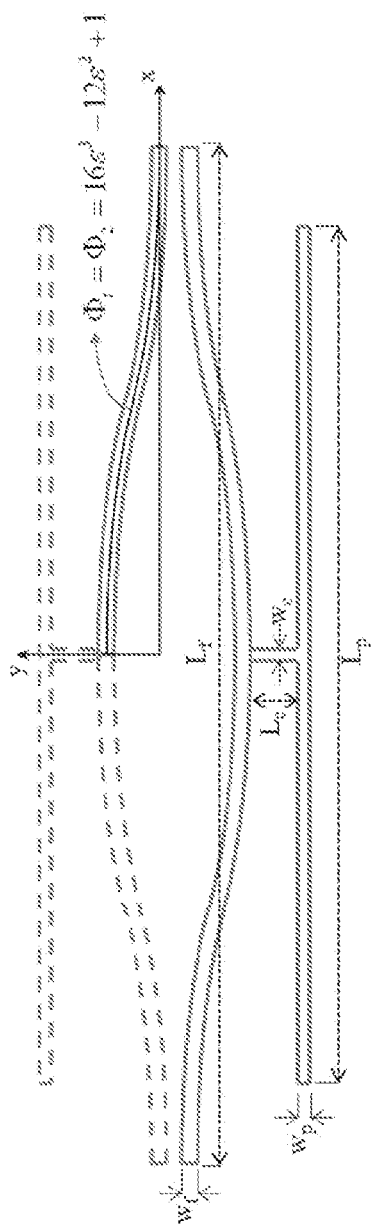
FIG. 2 illustrates an exemplary tine for use with the present system, according to one embodiment.

In the operation of the DETF force sensor, the basic mechanical parameter affected by the axial load is the equivalent spring constant. For very low damping, the natural frequency of the out-of-phase mode shape (FIG. 2) in the absence of axial load can be written as:

$$\omega_{n,0} = \sqrt{\frac{k_{eff,0}}{m_{eff,0}}} = \sqrt{\frac{192\frac{EI}{L_f^3}}{\frac{13}{95}\rho h w_f L_f + \rho h(w_p L_p + w_c L_c)}} \quad (1)$$

where $k_{eff,0}$ is the equivalent spring constant at zero axial load, $m_{eff}$ is the equivalent mass, EI is the flexural stiffness of each tine, $\rho$ is the materials mass density, h is the thickness of the device, $L_f$ and $w_f$ are the tine length and width, $L_p$ and $w_p$ are the capacitive plate length and width, and $L_c$ and $w_c$ are the connector bar length and width, respectively. Equation (2) predicts the operation frequency of the DETF.

According to one embodiment of the present system, the tuning fork is anchored 103 on one side and connected with a roller 105 on the opposite side. The external load is applied to the roller at a tip 106, which is designed to provide minimal resistance to axial loading; the axial component of the applied force is then nearly entirely transmitted to the tuning fork, while any non-axial components are absorbed by the roller, guaranteeing near perfect load alignment, and hence exceptional robustness. The efficacy of this roller guide mechanism was verified with a set of finite elements analyses.

When an axial load, $F_{appl}$, is applied to the roller, the resonance frequency shifts to:

$$\omega_n = \sqrt{\frac{k_{eff}}{m_{eff}}} = \sqrt{\frac{192\frac{EI}{L_f^3} + 2.4\frac{F_{appl}}{L_f}}{\frac{13}{95}\rho h w_f L_f + \rho h(w_p L_p + w_c L_c)}} = \sqrt{\omega_{n,0}^2 + 2.4\frac{F_{appl}}{m_{eff} L_f}} \quad (2)$$

Note that $F_{appl}$ is equal to twice the force applied on each tine. The scale factor (rate of change of the frequency of this mode with respect to axial loading) is then:

$$\frac{\partial \omega_n}{\partial F_{appl}} = \frac{1.2}{m_{eff} L_f \sqrt{\omega_{n,0}^2 + 2.4\frac{F_{appl}}{m_{eff} L_f}}} \quad (3)$$

In the absence of the applied load, the scale factor reduces to:

$$\alpha_0 = \frac{\partial \omega_n}{\partial F_{appl}}\bigg|_{F_{appl}=0} = \frac{1.2}{m_{eff} L_f \omega_{n,0}} \quad (4)$$

Considering all the parameters constant except for the loading force, the scale factor increases as the compressive loading increases, and approaches zero as the tensile loading increases (compressive loads are negative by convention). Substituting Eq.4 in Eq.2, the force-frequency relation can be written as:

$$\omega_a = \sqrt{\omega_{a,0}^2 + 2\alpha_0 \omega_{a,0} F_{appl}} \quad (5)$$

Hence, the tip loading can be found as:

$$F_{appl} = \frac{\omega_n^2 - \omega_{n,0}^2}{2\alpha_0 \omega_{n,0}} \quad (6)$$

Equation 6 directly relates the resonance frequency to tip loading. This simple relation also helps calibrating the device with only two parameters: the resonance frequency and the scale factor, both at unloaded conditions. Details of the calibration procedure are provided below.

Figure 3:
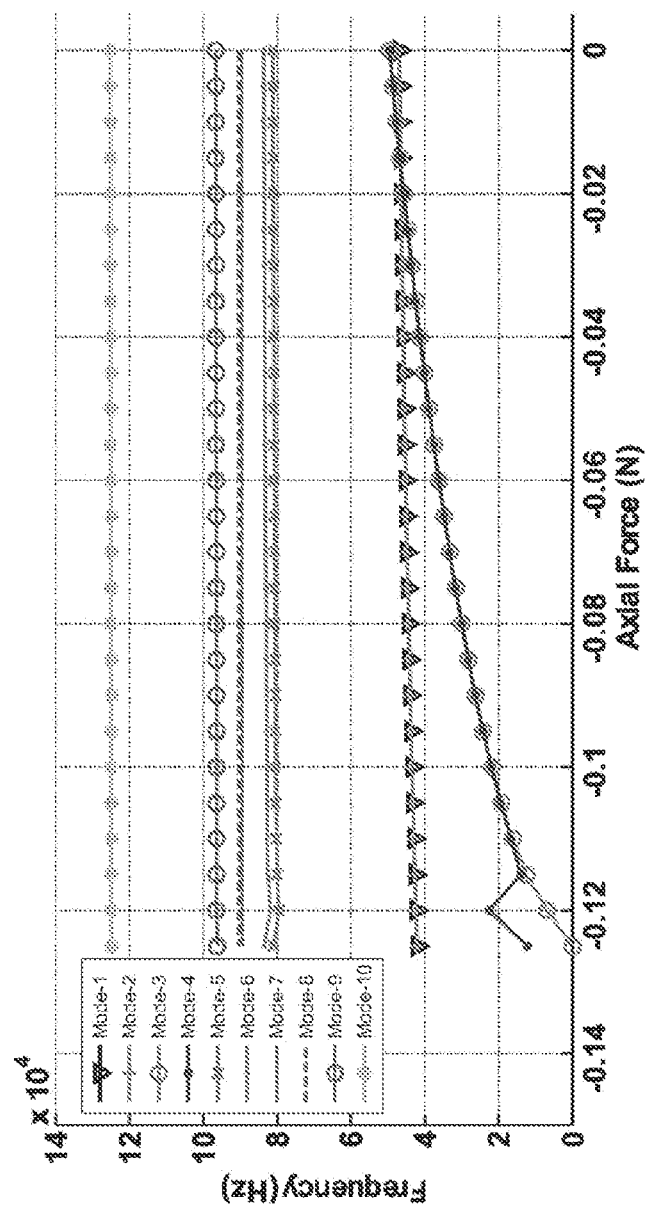
FIG. 3 illustrates exemplary natural frequency vs. axial loading for modes of an embodiment of the present system.
Figure 4:
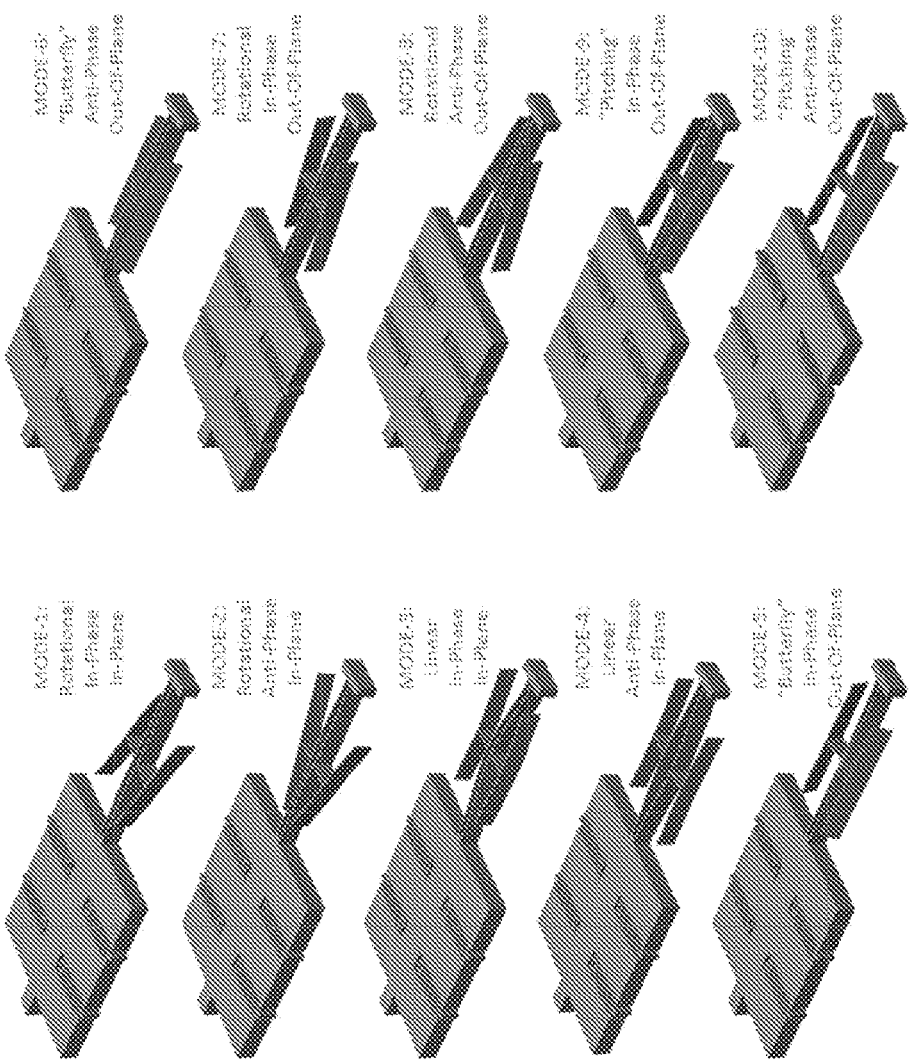
FIG. 4 illustrates zero mode shapes for simulations of exemplary embodiments of the present system.

FIG. 3 illustrates exemplary natural frequency vs. axial loading for modes of an embodiment of the present system. FIG. 4 illustrates zero mode shapes for simulations of exemplary embodiments of the present system.

To verify the operational range of the sensor with the roller structure in the proposed implementation, three dimensional finite elements simulations were performed. FIG. 3 illustrates the axial loading versus frequency for the first 10 modes; the corresponding mode shapes are depicted in FIG. 4. The preferred operational mode for the DETF is the out-of-phase mode (mode 4 in FIG. 4) due to its superior tip stability and overall anchor dissipation. The results clearly show that different modes exist with very similar frequencies. These "sibling" modes are a result of the symmetric structure of the DETF sensor. For example, the first two modes have nearly identical force-frequency trajectories, and the mode shapes are theoretically the same, albeit with opposite phases. The same is true for modes 3 and 4, which maintain nearly identical trajectories all the way to buckling (the erratic behavior of mode 4 near the buckling load is attributed to numerical inaccuracies). It is important to emphasize that the in-phase mode (mode 3) has a slightly lower frequency than the out-of-phase mode (mode 4), due to the slight difference in the effective stiffness near the boundaries. This has implication on the operation near the buckling load, as discussed below. It is possible that the erratic behavior in the mode 4 trajectory near the buckling load (FIG. 3) is due to numerical difficulties in resolving two very close resonant modes near the onset of buckling. This behavior is not observed experimentally (see explanation below).

The finite elements analyses depicted in FIGS. 3 and 4 reveal two potential problems: (i) the operating mode (mode 4) is very close in frequency to the sibling in-plane mode for the entire useful force range, and (ii) the frequency-force trajectories of modes 1-2 and 3-4 cross at an applied compressive force of ~20 mN. In principle, both features might confuse a detection system based on frequency locking. In practice, carefully balanced actuation solves both problems, as illustrated below.

Figure 5:
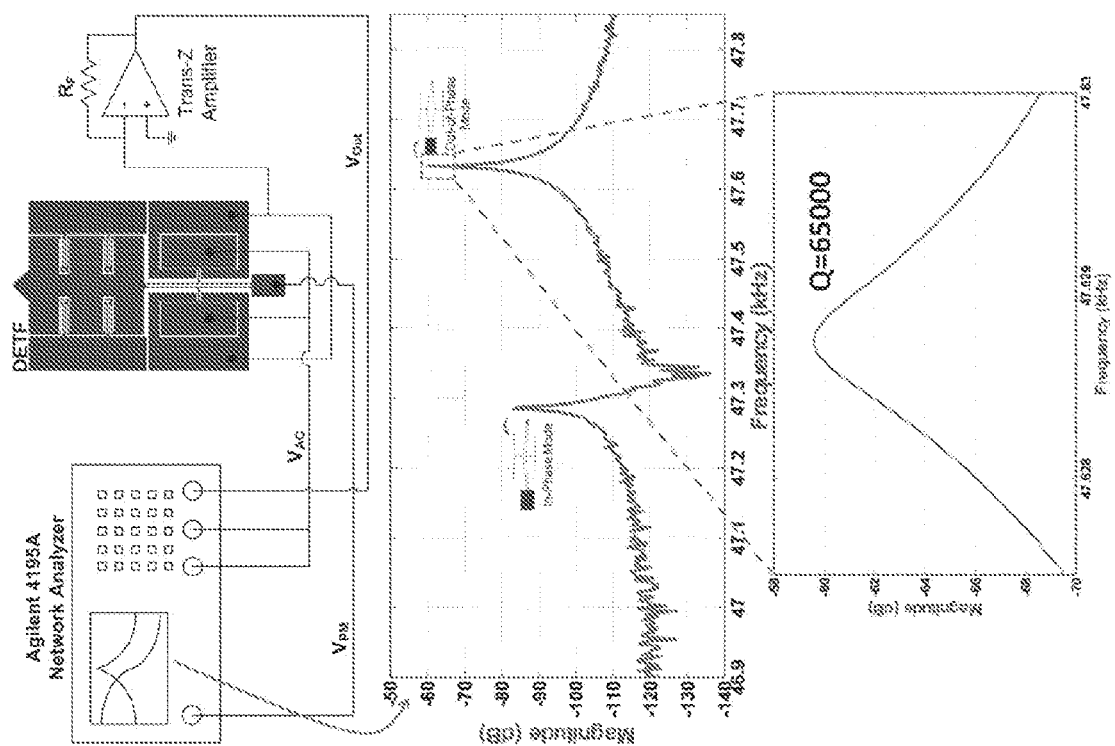
FIG. 5 illustrates an exemplary test setup and frequency response of a DETF sensor for use with the present system, according to one embodiment.

FIG. 5 illustrates an exemplary test setup and frequency response of a DETF sensor for use with the present system, according to one embodiment. Consider the frequency sweeps at zero load illustrated in FIG. 5, which are performed using a HP 4195A Network/Spectrum Analyzer with a LF353 OpAmp Trans-impedance stage with 1 MΩ feedback resistor, in vacuum (2.7 mTorr) and with a proof mass voltage of 40 V. The effect of the feed-through capacitance is eliminated by a calibration run. Note that, due to balanced excitation, the gain difference between two modes is significant (>20 dB), and the quality factor of the operational mode is above 60,000. This guarantees locking on the desired mode. In theory, the in-phase mode can be eliminated entirely by perfectly symmetrical driving (whereby the forcing signal on the two tines has no phase difference); in practice, any geometric or chip/substrate bonding asymmetry would make it appear. A balanced actuation is crucial, as the frequency separation of the two modes is very small (for the geometry under consideration, the measured in-phase mode has a natural frequency of 47.28 kHz, versus a frequency of 47.63 kHz for the out-of-phase mode). It should also be noted that these are the first modes visible with balanced excitation and detection of the parallel plate structure, implying that modes 1 and 2 are not interfering at zero load.

Furthermore, the large force test results presented herein show that the crossing of mode pair 1-2 and mode pair 3-4 at 20 mN does not affect the operation of the DETF, thanks to balanced actuation.

Figure 6:
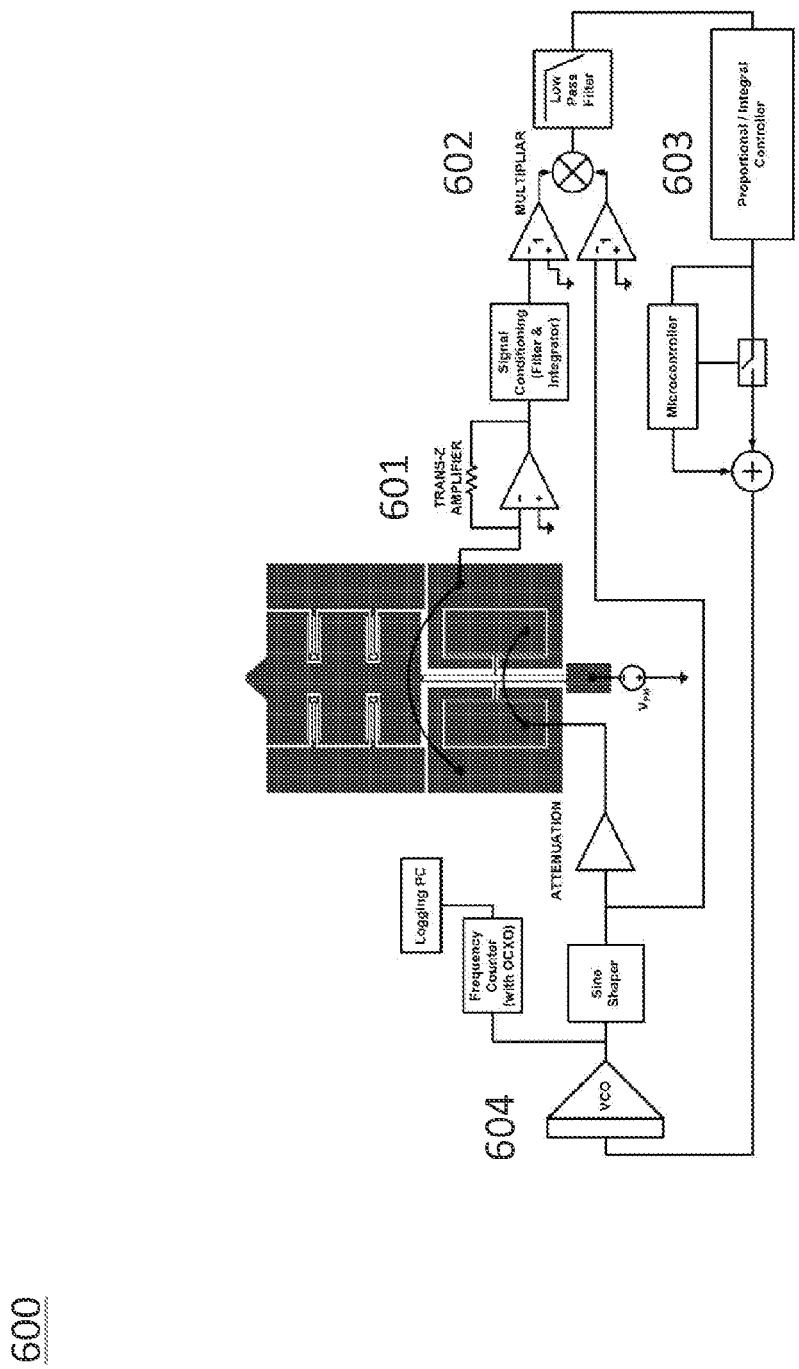
FIG. 6 illustrates a schematic of an exemplary PLL for use with the present system, according to one embodiment.

FIG. 6 illustrates a schematic of an exemplary PLL for use with the present system, according to one embodiment. Detection of frequency changes upon external load application is performed via a Phase-Locked-Loop (PLL) circuit, implemented by discrete components on a custom-designed compact PCB. Compared to alternative approaches like self-resonance or amplitude detection, the PLL circuit offers unique flexibility in selecting the desired resonance mode of operation with better control in operational parameters like detection bandwidth and range. As DETF resonators have multiple Eigen modes and the bandwidth requirement for quasi-static mechanical characterizations is not very demanding, a low speed—thus stable—PLL implementation is the best choice as a control scheme. The PLL circuit 600 comprises four main blocks: a pre-amplifier stage 601, a phase detector 602, a controller 603, and a Voltage-Controlled-Oscillator (VCO) 604. The VCO output is a 500 mV peak-to-peak sinusoid which is attenuated and connected to the drive plates. The current pumped by the sense plates, which is proportional to the velocity of the tines, is fed into the trans-impedance amplifier (TIA) and converted into voltage. This signal is then cleared from offsets, shifted 90° in phase to compensate for the differentiator effect of capacitive detection, and fed into a phase detector composed of a multiplier (AD630) and a low-pass filter. The multiplier has the other input coming from the drive signal. Thus the signal at the end of the low-pass filter is proportional to the cosine of the phase angle between the drive and the sense signals. The proportional-integral (PI) controller adjusts the VCO (EXAR2206) frequency so that this phase difference between the excitation signal and the TIA output locks to 0°, thus achieving resonance. Here the bandwidth of the PLL is set by the PI controller, and it is designed to be 1 Hz.

Although an amplitude controller would improve the robustness of an analog (sinusoidal) PLL for a limited frequency range, it complicates the operation when the resonance frequency of the sensor changes considerably. Since the TIA output signal amplitude is proportional to the tine velocity (not its displacement), a drastic change in the resonance (or operation) frequency would result in drastic changes in the vibration amplitude. As this is undesirable, it was decided to maintain the VCO output amplitude constant. Thus, the VCO output amplitude is attenuated with a fixed negative gain to a safe level of 5 mV (to avoid elastic non-linearities possibly induced by excessive vibration amplitude) and directly fed to the DETF drive plates.

Electrostatic driving of the tines reduces their operational frequency by introducing a negative stiffness term in Eq. (2) (electrostatic softening). The operational resonance frequency of the overall loop can then be written as:

$$\omega_{n,op} = \sqrt{\frac{192\frac{EI}{L_f^3} + 2.4\frac{F_{appl}}{L_f} - \frac{\varepsilon_0 h L_p}{g^3}\left(V_{DC}^2 + \frac{V_{AC}^2}{2}\right)}{\frac{13}{95}\rho h w_f L_f + \rho h(w_p L_p + w_c L_c)}} \quad (7)$$

where $V_{DC}$ is the DC polarization voltage applied to the DETF body and the VAC is the actuation voltage applied to the drive tines. All other parameters are the same as in Equation 2. One should also note that any change in the actuation amplitude also affects the resonance frequency, clearly showing that keeping the actuation voltage constant (i.e., avoiding an amplitude controller) is essential for resonant force sensors.

One aspect of the PLL-MEMS integration is the active frequency range and the PLL startup procedure. The startup frequency of the VCO is much more vital in MEMS applications than is for the PLL's used in digital devices. The source of the problem is that the resonator response is below the noise level if the excitation frequency is not in the active range of the resonator. To illustrate this, consider the frequency sweep in FIG. 5. The out-of-phase mode has a resonant frequency at 47,628.7 Hz and the resonator response drops down to the noise level for frequencies outside of the 47,500-47800 Hz range. This range represents the active frequency range of the resonator. If the VCO startup frequency is outside of this range, the PLL cannot excite the resonator, and thus cannot lock. To overcome this problem, a microcontroller external to the PLL PCB is utilized to sweep a band of frequencies at startup while monitoring the error signal (the LPF output). When the error signal is 0V (meaning that the PLL has already locked), the sweep is stopped, transferring control to the PLL. The microcontroller also monitors the controller output for the case of saturation and shifts the VCO range accordingly, yielding a resonant load cell with a wide operable frequency range.

Figure 7:
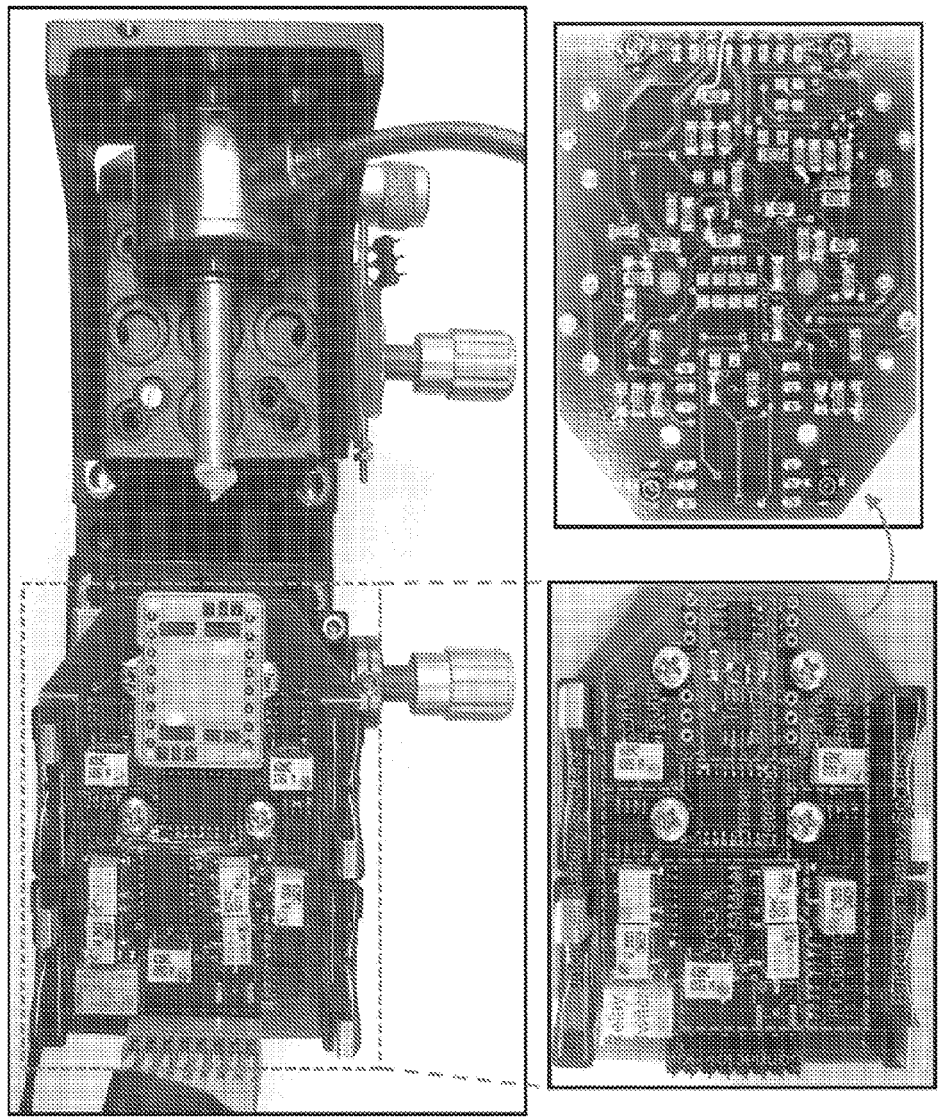
FIG. 7 illustrates placement of discrete elements on a printed circuit board, according to one embodiment of the present system.

FIG. 7 illustrates placement of discrete elements on a printed circuit board, according to one embodiment of the present system. The figure shows the placement of the discrete components on the 65 mm×52 mm Printed Circuit Board (PCB), which also supports battery operation. Button cell batteries on the board proved to be a noise reducing aspect especially when high voltage piezo stage is in operation and very small forces are being measured.

Figure 8:
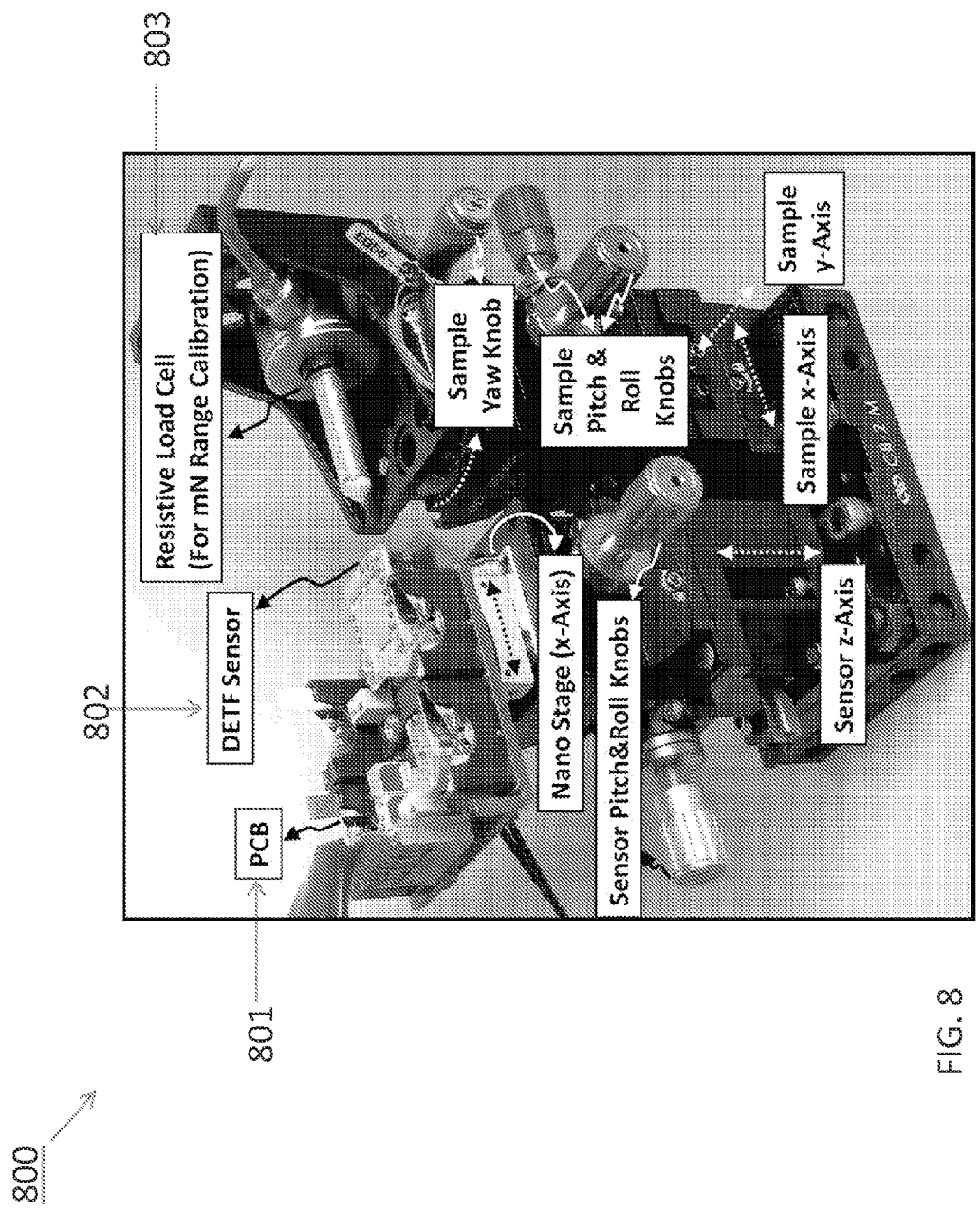
FIG. 8 illustrates an exemplary micro-mechanical test frame for use with the present system, according to one embodiment.

FIG. 8 illustrates an exemplary micro-mechanical test frame for use with the present system, according to one embodiment. It will be appreciated that the measurements and ranges described herein are one embodiment, and that multiple ranges and configurations are possible. According to one embodiment, the PCB 801 implementation of the PLL circuit described herein is mounted on a commercially available piezo displacement actuator with a 10 mm range and 50 nm resolution, according to one embodiment. Another closed-loop actuator with sub-nm resolution and 15 µm range can be added in series to the above actuator for utmost position control in terms of both resolution and range. The sensor 802 is mounted on a 4-axis sensor stand, and the sample is placed on the 5-axis sample stand for precise alignment with the load cell 803. The redundant degrees of freedom are for both alignment and imaging purposes.

The entire test frame is inserted in a vacuum chamber, for maximum resolution. Direct imaging of the experiment is easily achievable with a long working distance lens; alternatively, the entire test frame can be operated within a scanning electron microscope (SEM).

Figure 9:
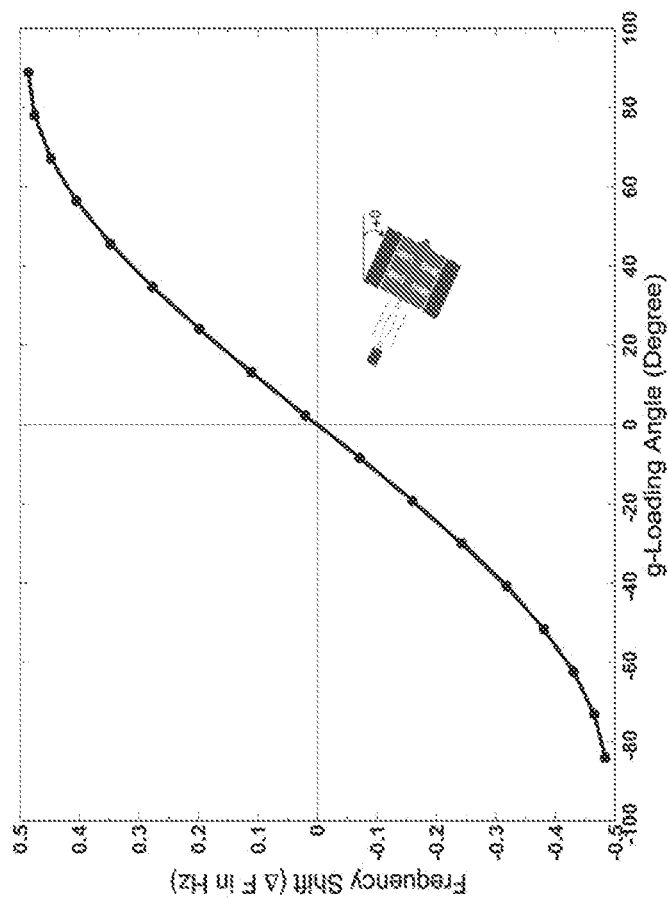
FIG. 9 illustrates frequency shift for a g-test of an embodiment of the present system.
Figure 10:
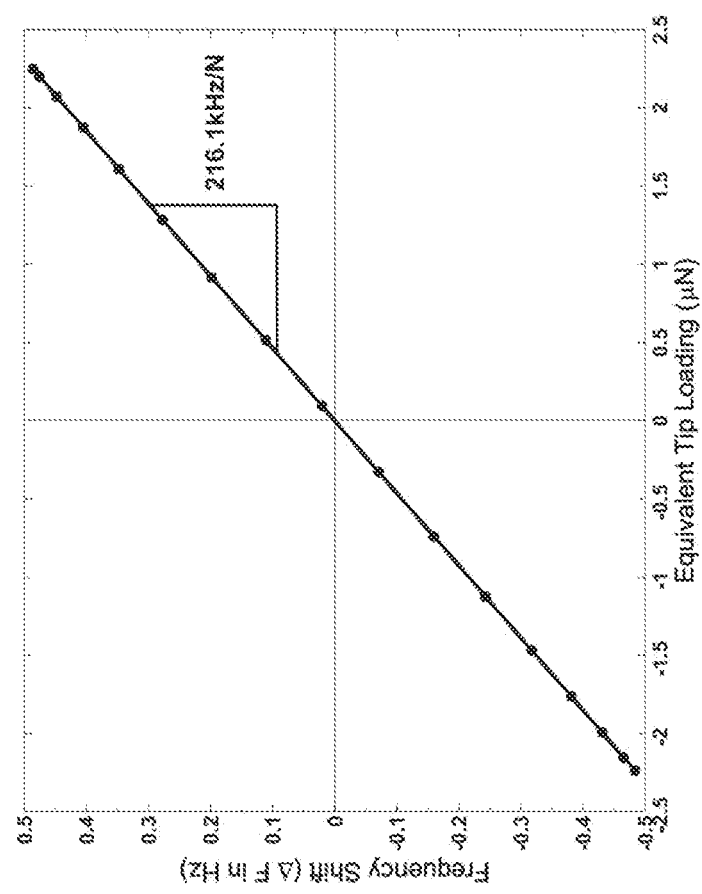
FIG. 10 illustrates experimentally measured frequency shift versus equivalent tip loading obtained from FIG. 9.

FIG. 9 illustrates experimentally measured frequency shift of a tuning fork of an embodiment of the present system. FIG. 10 illustrates frequency shift for a g-test of an embodiment of the present system. To characterize an exemplary implementation of the present system, a g-test was performed by rotating the sensor about its out-of-plane axis—thus using the roller as a suspended mass—and measuring the change in natural frequency of the fork (FIG. 9). When the gravitational force on the tuning fork is computed as $F_g = m_{roller} g \sin \theta$, a force range between −2.25 and +2.25 µN is probed, and a sensitivity of 216.1 kHz/N is obtained (FIG. 10).

Figure 11:
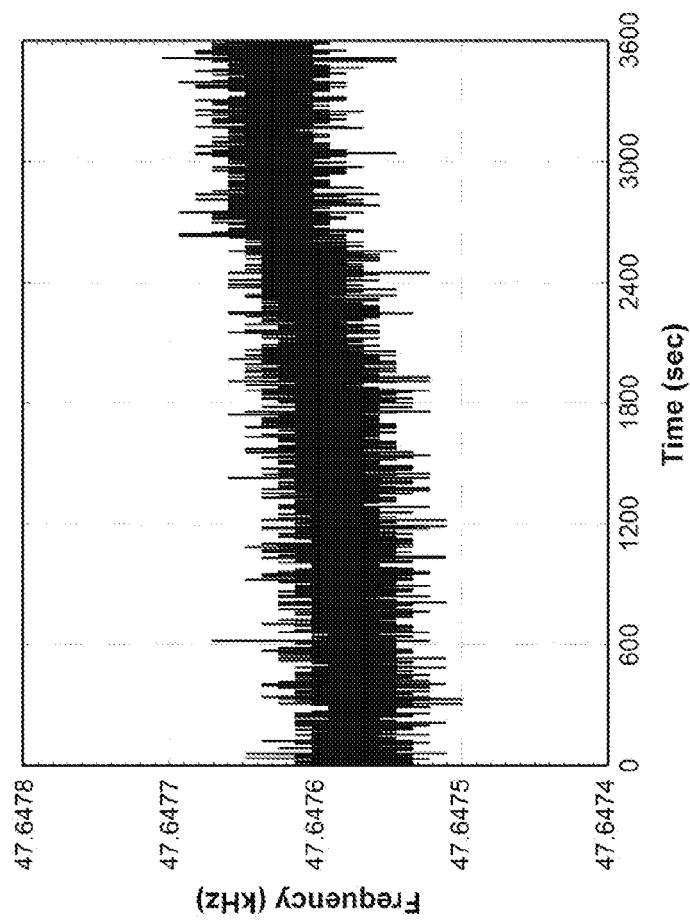
FIG. 11 illustrates an exemplary one-hour long frequency drift of an exemplary embodiment of the present system.
Figure 12:
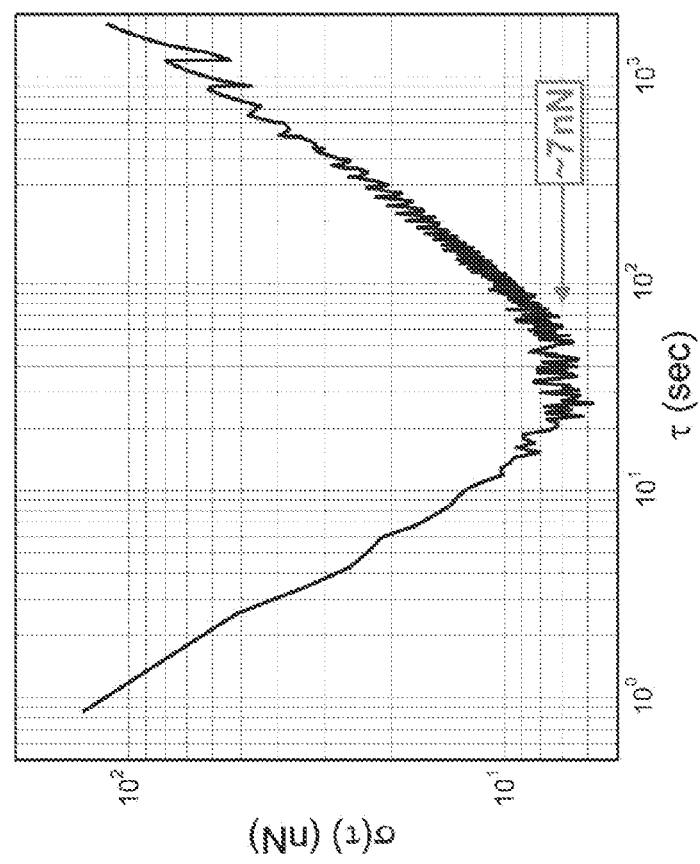
FIG. 12 illustrates an Allan variance analysis on the data reported in FIG. 11.

FIG. 11 illustrates an exemplary one-hour long frequency drift of an exemplary embodiment of the present system. FIG. 12 illustrates an Allan variance analysis on the data reported in FIG. 11. To experimentally investigate the maximum achievable force resolution, the frequency data is acquired over 3600 seconds (1 hour) at a sampling rate of 1.18 sample/sec (corresponding to a sampling time of 0.85 seconds) in FIG. 11. The data was collected using a 32-bit counter with an oven stabilized quartz reference. With the help of Allan variance analysis, resolutions as low as 7 nN are demonstrated at a frequency integration time of ~20 seconds (FIG. 12). Tests are conducted without any temperature compensation at an average ambient temperature of 22° C.

Figure 13:
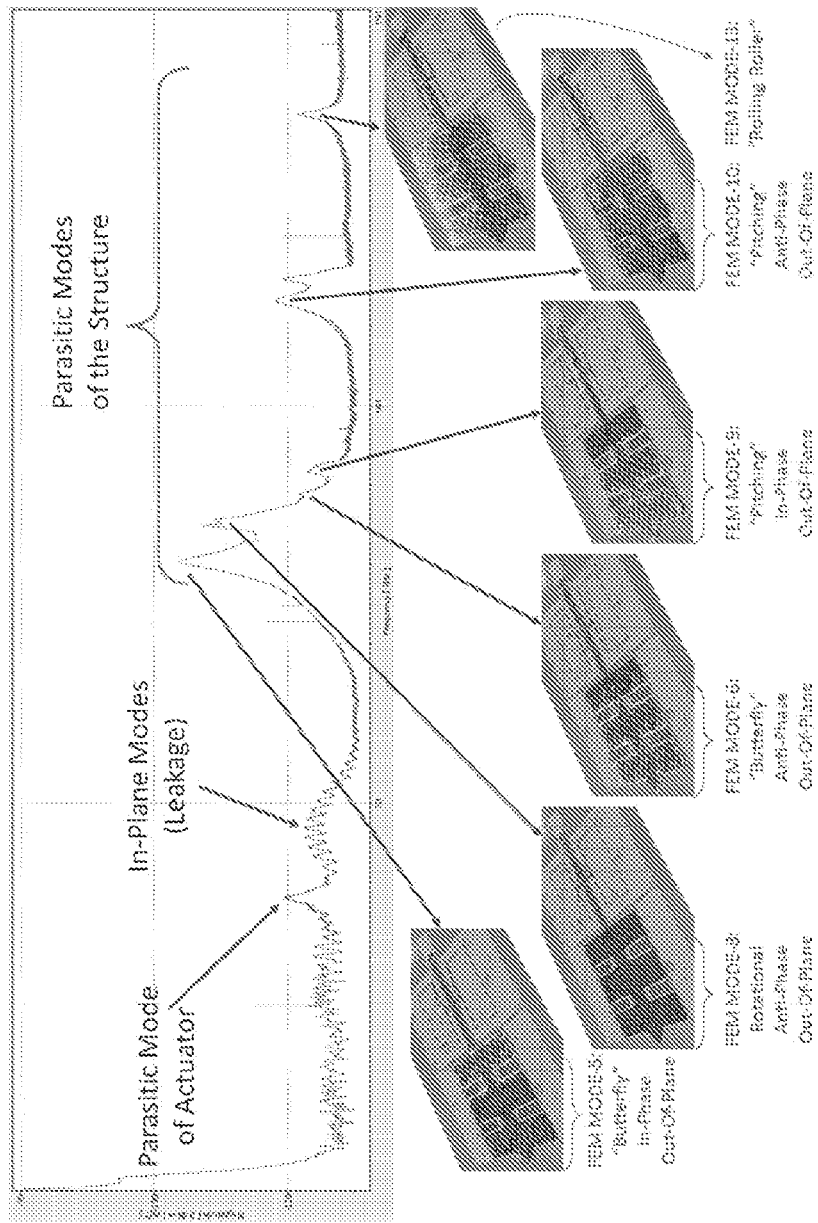
FIG. 13 illustrates a measured average spectrum of structural out-of-plane modes of an exemplary embodiment of the present system.

FIG. 13 illustrates an average spectrum of structural out-of-plane modes of an exemplary embodiment of the present system. An investigation of the parasitic out-of-plane-modes of the device was conducted with a Polytec MSA-500 Scanning Laser Doppler Vibrometer, to confirm that the frequency range of the DETF for the 0-0.085N compressive load range is free of parasitic modes. As Finite Elements analyses provide the frequency dependence of all the parasitic modes (FIG. 3), a zero-load investigation is sufficient. FIG. 13 shows the average spectrum of the structural out-of-plane modes alongside the measured mode shapes. The results agree reasonably well with the FEM simulation results in FIGS. 3 and 4, both in terms of mode sequence and Eigen frequency values.

The only discrepancy is the rotational anti-phase mode (mode 8), which shows a lower frequency then predicted by FEM, possibly due to undercuts during the fabrication step. The emphasis should be put on the fact that the frequencies of these out-of-plane modes are away from the in-plane and out-of-phase operational mode, and the same conclusion applies in the presence of axial loads in the 0-0.085N range.

The g-test method described above can also be used for calibration purposes. Calibration is essential to correct for manufacturing imperfections and if mechanical experiments require characterization at different temperatures. Temperature changes affect a DETF force sensor output by modifying three parameters: offset (i.e. zero-load) frequency, scale factor, and noise level. The offset frequency is altered by changes in dimensional quantities (beam lengths and widths and gap sizes) and thermo-mechanical stresses (induced by differences in thermal expansion coefficients of the device layer, substrate, and package). Incidentally, changes in the ambient pressure can also significantly affect the offset frequency. The scale factor is mostly distorted by thermally induced geometric changes in the tine cross-section.

According to one embodiment, the present system adopts a low-cost calibration method that can correct the offset and scale factor differences at different temperatures, thus expanding the application of this sensor to a wide temperature band. For calibration, two parameters are required: the zero-load resonance frequency, $\omega_{n,0,op}$, and the zero-load scale factor, $\alpha_{0,op}$. Equation 6 can be rewritten as:

$$F_{appl} = \frac{\omega_{n,op}^2 - \omega_{n,0,op}^2}{2\alpha_{0,op}\omega_{n,0,op}} \tag{8}$$

which provides a calibration curve. The validity of Equation 8 is demonstrated in FIG. 14.

Figure 14:
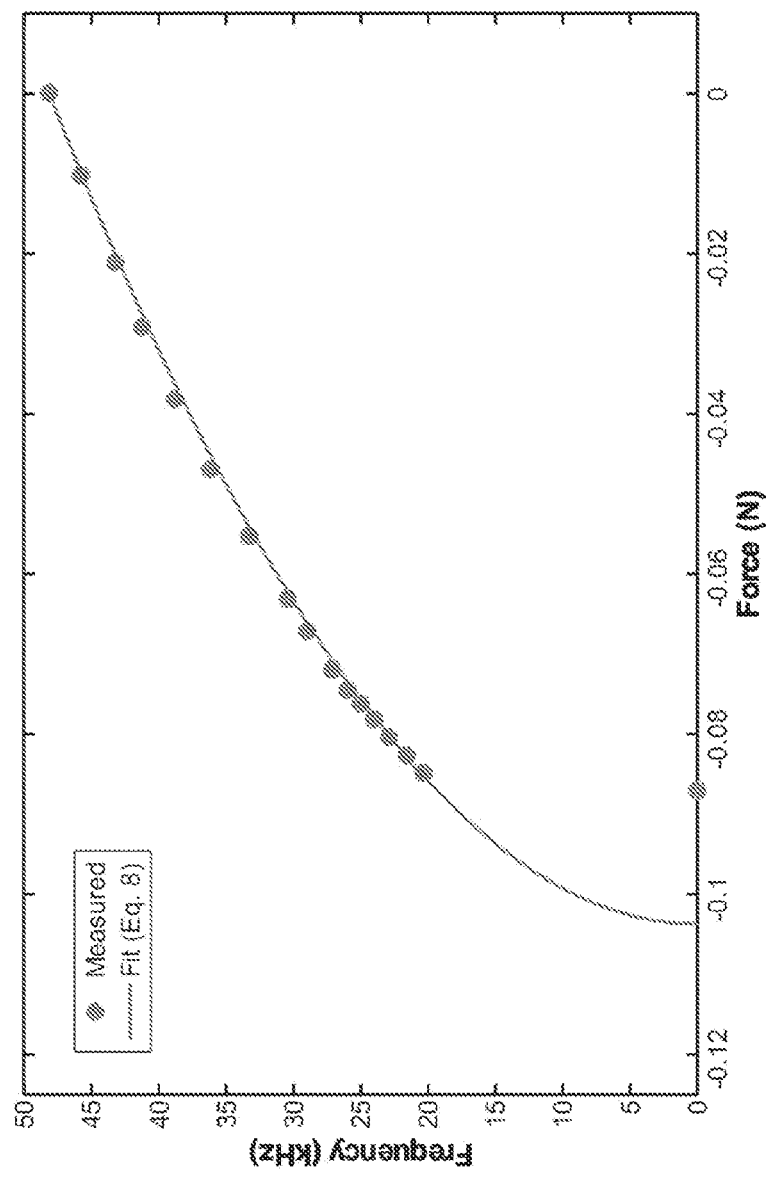
FIG. 14 illustrates a frequency-force plot for a full-range load test using the present system, according to one embodiment.

FIG. 14 illustrates a frequency-force plot for a full-range load test using the present system, according to one embodiment. The test frame actuator was used to push the load cell against an external commercially available resistive load cell (Sensotec 31/1435-01, 250 g range). The shifts in resonant frequency were detected by the PPL circuit described in Sec.

3, whereas the load was measured by the external load cell. For application of Eq. (8), the zero load resonance frequency and the zero load scale factor were obtained by the g-test described above (hence requiring no external apparatus). Remarkably, Eq. (8) is in excellent agreement with the experimental results over the entire operational range of the device (0-80 mN in compression). The important conclusion is that the proposed load cell requires no external calibration instrument to correct for manufacturing imperfections and/or changes in the operating temperature; it is sufficient to perform a g-test with the device immediately prior to its use to obtain $\omega_{n,0,op}$ and $\alpha_{0,op}$. During the experiment, the force can then be obtained as a function of the detected frequency change via Eq. (8). Notice that the calibrated frequency/force curve predicts buckling for the operational (out-of-phase) mode at a compressive load of ~105 mN, approximately 15% lower than predicted by Finite Elements analysis (FIG. 3). This difference is entirely attributed to manufacturing imperfection and confirms the important of the robust calibration approach presented herein. At the same time, the experimental results show evidence of in-phase buckling (and pull-in) at a compressive load as low as 90 mN. Such a large separation in the in-phase and out-of-phase buckling modes is not predicted by the FE analyses, but can be explained by a slight asymmetry in the loading conditions (whereby one tine is slightly more stressed than the other).

Figure 15:
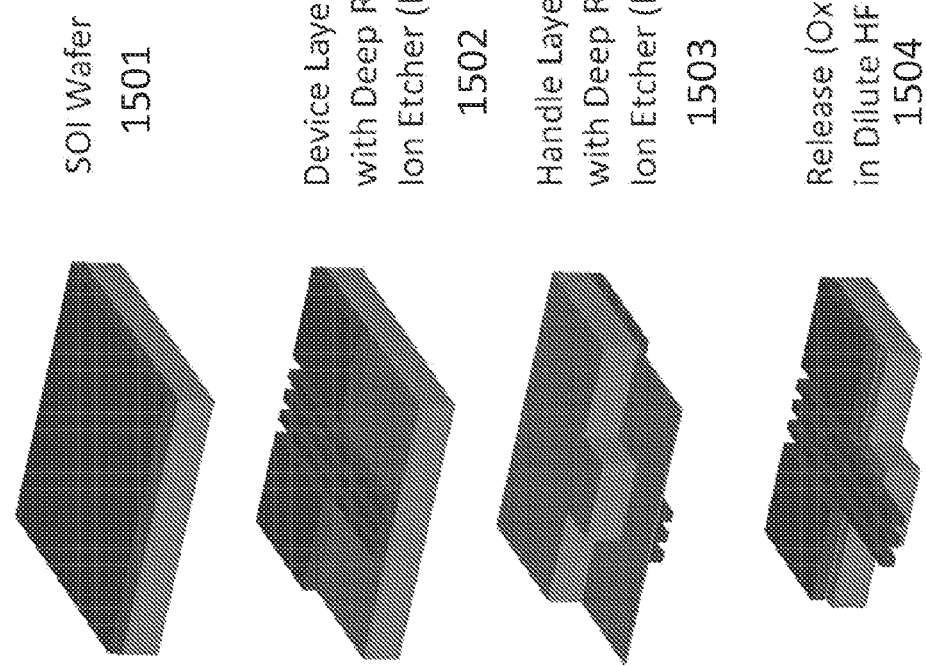
FIG. 15 illustrates a schematic of an exemplary silicon-on-insulator manufacturing process for use with the present system, according to one embodiment.

FIG. 15 illustrates a schematic of an exemplary silicon-on-insulator manufacturing process 1500 for use with the present system, according to one embodiment. The etch of the wafer 1501 requires etch of the device layer first 1502. After cleaning the photoresist residues, the whole wafer is flipped and attached to a secondary handle wafer for the back side etching 1503. Some thermal grease is applied between the wafers, on the peripheries only.

After the backside etch, the secondary handle wafer is separated carefully from the device wafer and thoroughly cleaned 1504 in warm acetone and piranha (%50 $H_2O_2$, %50$H_2SO_4$) solutions.

In this process, a new layout method is also implemented to eliminate the requirement of a dicing procedure: dicing is problematic because the harsh cooling may easily destroy the thin extruded tips, tines and electrostatic plates. Since the process involves a handle layer etch, all the individual dies are connected to silicon branches with 100μ×100μ pieces (for example). These pieces of silicon keep the dies together after the backside etch and during the cleaning, and enable easy removal of the die when needed, eliminating the need for dicing altogether.

Figure 16:
FIG. 16 illustrates an exemplary cleaned device wafer with ready to pick devices, according to one embodiment of the present system.

FIG. 16 illustrates an exemplary cleaned device wafer according to one embodiment of the present system. The cleaned device wafer 1600 includes ready-to-use devices.

Figure 17:
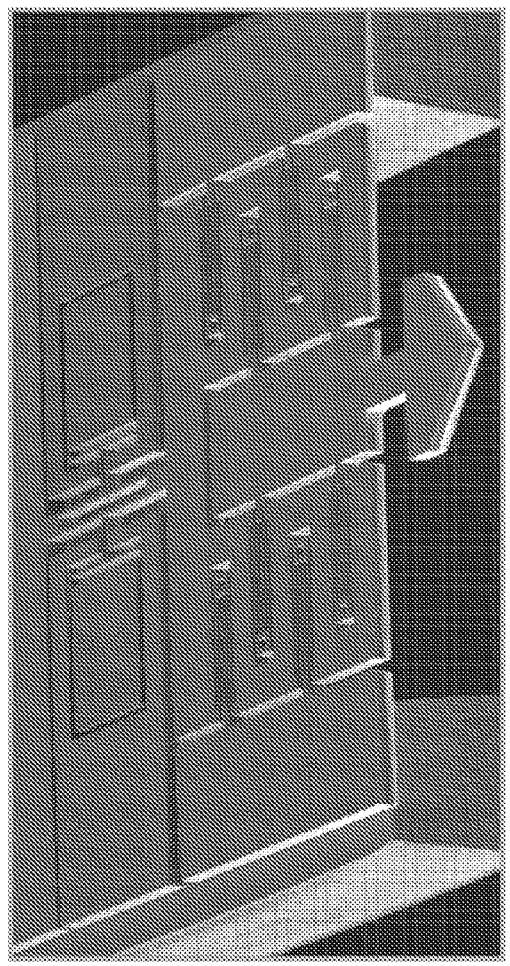
FIG. 17 illustrates an SEM image of an exemplary fabricated DETF sensor using the exemplary silicon-on-insulator process according to one embodiment of the present system.

FIG. 17 illustrates an SEM image 1700 of an exemplary fabricated DETF sensor using the exemplary silicon-on-insulator process according to one embodiment of the present system. With the backside etch, the handle layer under the DETF structure can also be removed, enabling more thorough cleaning of the device and resulting in higher yield.

Figure 18:
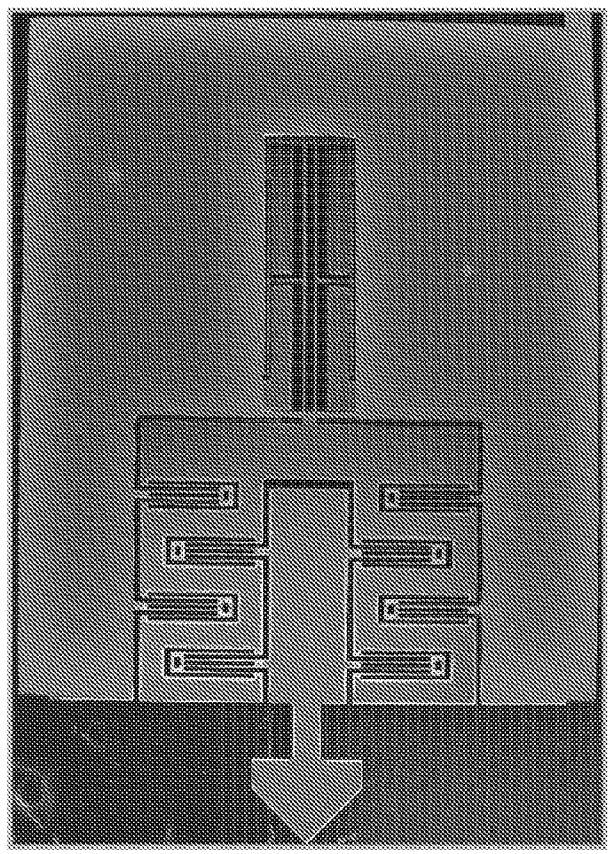
FIG. 18 illustrates a backside view of an exemplary fabricated DETF sensor using the exemplary silicon-on-insulator process according to one embodiment of the present system.

FIG. 18 illustrates a backside view 1800 of an exemplary fabricated DETF sensor using the exemplary silicon-on-insulator process according to one embodiment of the present system. The backside view of the force sensor can be seen, with the 100 μm×100 μm attachment piece at the lower right corner. The opening below the DETF region has two purposes; better cleaning and more balanced electrostatics. Since the handle layer is grounded, having a ground plane right under the DETF causes an imbalance in the electrostatics, and induces a downward force due to electrostatic attraction. Removing the handle layer beneath the DETF solves this problem.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

Self calibrating micro-fabricated load cells have been disclosed. It is understood that the embodiments described herein are for the purpose of elucidation and should not be considered limiting the subject matter of the disclosure. Various modifications, uses, substitutions, combinations, improvements, methods of productions without departing from the scope or spirit of the present invention would be evident to a person skilled in the art.

What is claimed is:
1. A self calibrating load cell, comprising:
   a resonant double ended tuning fork force sensor; and
   a phase locked loop circuit for detection of frequency changes upon external load application to the resonant double ended tuning fork force sensor;
   wherein the resonant double ended tuning fork sensor has a zero-load resonance frequency ($\omega_{n,o,op}$) and a zero-load scale factor ($\alpha_{o,op}$); and
   wherein, during calibration, a load on the resonant double ended turning fork force sensor is obtained according to a calibration curve equation: $F_{appl}=(\omega_{2n,0p}-\omega^2_{n,o,0p})/(2*\alpha_{o,op}*\omega_{n,o,0p})$.

2. The self calibrating load cell of claim 1, wherein the resonant double ended tuning fork force sensor comprises
   at least one sense electrode;
   at least one drive electrode;
   a resonant tuning fork;
   a spring supported roller; and
   a load cell tip for application of the external load.

3. The self calibrating load cell of claim 2, wherein the spring supported roller is situated between the resonant tuning fork and the load cell tip.

4. The self calibrating load cell of claim 1, wherein the phase locked loop circuit comprises
   a pre-amplifier stage;
   a phase detector;
   a controller; and
   a voltage controlled oscillator (VCO).

5. The self calibrating load cell of claim 1, wherein the resonant double ended tuning fork force sensor and a phase locked loop circuit are assembled on a printed circuit board (PCB).

6. The self calibrating load cell of claim 5, wherein the PCB dimensions are 65 mm×52 mm.

7. The self calibrating load cell of claim 1, wherein the resonant double ended tuning fork force sensor is implemented with a silicon-on-insulator (SOI) process with 100 μm silicon structural layer.

8. The self calibrating load cell of claim 7, wherein the silicon-on-insulator (SOI) process comprises:
   etching a device layer of a wafer;
   removing photoresist residues from the wafer;
   attaching the wafer to a secondary handle wafer and etching the backside of the wafer;
   removing the secondary handle wafer from the device wafer;
   cleaning the device wafer; and
   separating the devices without dicing.

9. The self calibrating load cell of claim 1, wherein the resonant double ended tuning fork force sensor has a resolution of up to 7 nN and a compressive load range of up to 0.085N, exceeding a dynamic range of 140 dB (100 parts per billion).

10. The self calibrating load cell of claim 1, wherein the resonant double ended tuning fork force sensor has a scale factor of 216 kHz/N, a Q-factor greater than 60,000 at 3 mTorr ambient pressure and a zero load resonant frequency of up to 47.6 kHz.

11. A method of characterization, comprising:
   calibrating a resonant double ended tuning fork sensor, wherein the calibrating comprises
      performing a load test with the resonant double ended tuning fork force sensor prior to its use to obtain a zero-load resonance frequency ($\omega_{n,o,op}$) and a zero-load scale factor ($\alpha_{o,op}$); and
      during application of external force, obtaining the zero-load resonance frequency ($\omega_{n,o,op}$) and zero-load scale factor ($\alpha_{o,op}$) as a function of detected frequency change;
   applying external axial force (compressive or tensile) to a resonant double ended tuning fork force sensor, wherein a natural frequency of tines of resonant double ended tuning fork force sensor decreases or increases in response to the applied external axial force; and
   detecting the decrease or increase in natural frequency by means of a circuitry comprising a phase locked loop circuit;
   wherein, during calibration, a load on the resonant double ended turning fork force sensor is obtained according to a calibration curve equation: $F_{appl} = (\omega_{2n,0p} - \omega^2_{n,o,0p})/(2*\alpha_{o,op}*\omega_{n,o,0p})$.

12. The method of claim 11, wherein the resonant double ended tuning fork force sensor comprises:
   at least one sense electrode;
   at least one drive electrode;
   a resonant tuning fork;
   a spring supported roller; and
   a load cell tip for application of the external load.

13. The method of claim 11, wherein the phase locked loop circuit comprises:
   a pre-amplifier stage;
   a phase detector;
   a controller; and
   a voltage controlled oscillator (VCO).

14. The method of claim 11, wherein the phase locked loop circuit and resonant double ended tuning fork force sensor are assembled on a printed circuit board (PCB).

15. A load cell assembled on a printed circuit board (PCB), comprising:
   a force sensor; and
   a circuit for detection of frequency changes upon external load application to the force sensor;
   wherein the force sensor has a zero-load resonance frequency ($\omega_{n,o,op}$) and a zero-load scale factor ($\alpha_{o,op}$); and
   wherein, during calibration, a load on the resonant double ended turning fork force sensor is obtained according to a calibration curve equation: $F_{appl} = (\omega_{2n,0p} - \omega^2_{n,o,0p})/(2*\alpha_{o,op}*\omega_{n,o,0p})$.

16. The load cell of claim 15, wherein the force sensor is a resonant double ended tuning fork force sensor.

17. The load cell of claim 15, wherein the load cell is self calibrating.

18. The load cell of claim 15, wherein the force sensor is implemented using a silicon-on-insulator process.

* * * * *